United States Patent
Park et al.

(10) Patent No.: US 8,177,556 B2
(45) Date of Patent: May 15, 2012

(54) HEALING ABUTMENT AND DENTAL IMPLANT HAVING THE SAME

(75) Inventors: Kwang-Bum Park, Daegu (KR); Cheol-Woong Jeong, Gwangju (KR)

(73) Assignee: Megagen Co., Ltd., Gyeongsan-Si, Gyeongsangbuk-Do (KR)

( * ) Notice: Subject to any disclaimer, the term of this patent is extended or adjusted under 35 U.S.C. 154(b) by 260 days.

(21) Appl. No.: 11/559,245

(22) Filed: Nov. 13, 2006

(65) Prior Publication Data

US 2007/0275351 A1    Nov. 29, 2007

(30) Foreign Application Priority Data

May 29, 2006  (KR) ........................ 10-2006-0048108

(51) Int. Cl.
*A61C 13/12* (2006.01)
*A61C 13/225* (2006.01)
*A61C 8/00* (2006.01)

(52) U.S. Cl. ........................................ 433/173; 433/172

(58) Field of Classification Search .......... 433/172–176, 433/218–223
See application file for complete search history.

(56) References Cited

U.S. PATENT DOCUMENTS

| | | | | |
|---|---|---|---|---|
| 4,856,994 A | * | 8/1989 | Lazzara et al. | ................. 433/173 |
| 5,344,457 A | | 9/1994 | Pilliar et al. | |
| 5,368,483 A | * | 11/1994 | Sutter et al. | ................... 433/173 |
| 5,759,034 A | * | 6/1998 | Daftary | ........................ 433/173 |
| 6,168,436 B1 | * | 1/2001 | O'Brien | ........................ 433/173 |
| 6,227,856 B1 | * | 5/2001 | Beaty et al. | .................... 433/172 |
| 6,887,077 B2 | * | 5/2005 | Porter et al. | ................... 433/174 |
| 2006/0183078 A1 | * | 8/2006 | Niznick | ........................ 433/173 |

FOREIGN PATENT DOCUMENTS

| | | |
|---|---|---|
| EP | 1 118 312 A 2 | 7/2001 |
| JP | 2004-283552 | 10/2004 |
| WO | WO 98/32393 | 7/1998 |
| WO | WO 98/52490 | 11/1998 |
| WO | WO 99/04723 | 2/1999 |
| WO | WO 99/17676 | 4/1999 |
| WO | WO 00/02497 | 1/2000 |
| WO | WO 02/22038 | 3/2002 |

OTHER PUBLICATIONS

English Abstract for Publication No. 2004-283552.

* cited by examiner

*Primary Examiner* — Todd Manahan
*Assistant Examiner* — Matthew Nelson
(74) *Attorney, Agent, or Firm* — F. Chau & Associates, LLC (57) ABSTRACT

A healing abutment includes a main body portion and a coupling portion. The main body portion has an inclined section that is inclined such that at least a part of a gum contact portion that contacts a gum when coupled to a fixture that is implanted into an alveolar bone has an outer diameter that decreases from a lower end toward an upper end. The coupling portion is coupled to the main body portion to detachably couple the main body portion to the fixture.

9 Claims, 8 Drawing Sheets

HEALING ABUTMENT AND DENTAL IMPLANT HAVING THE SAME

CROSS-REFERENCE TO RELATED PATENT APPLICATIONS

This application claims the benefit of Korean Patent Application No. 10-2006-0048108, filed on 29 May 2006, in the Korean Intellectual Property Office, the disclosure of which is incorporated by reference herein in its entirety.

BACKGROUND OF THE INVENTION

1. Field of the Invention

The present invention relates to a healing abutment and a dental implant having the same, and more particularly to a healing abutment which can provide an implant operation result with an improved aesthetic feature and prevent intrusion of germs or foreign materials between gum and implant, and a dental implant having the same.

2. Description of Related Art

An implant is a replacement to human tissues when they are lost. For the specific field of dentistry, the implant is an artificial tooth. That is, the implant recovers the function of a tooth by placing a dental root in an alveolar bone where a tooth is removed, and fixing an artificial tooth to the implant. The implant may be made of titanium having no rejection symptoms when placed in a human body.

In the case of a general dental prosthesis or denture, surrounding teeth and bone are damaged as time passes. In contrast, the implant does not damage surrounding tooth tissues and causes no tooth decay while providing the same function and shape as a natural tooth. Thus, the implant can be used semi-permanently.

Also, the implant improves not only the restoration of a single lost tooth but also the function of the artificial teeth of partially toothless or completely toothless patients and enhances the aesthetic feature in the restoration of dental prosthesis. Furthermore, the implant can distribute excessive stress applied to the tissues of the surrounding support bone so as to help the stabilization of a row of teeth.

The implant operation performed in dentistry includes an operation step of implanting an implant into a gum bone, that is, the alveolar bone and a prosthesis step of installing an artificial tooth by connecting an abutment to the placed implant.

There may be a variety of implant operation methods. For example, for a fixture level impression method, a model of a mouth is completed by connecting impression coping in the mouth when an impression is obtained in the prosthesis step.

The alveolar bone undergoes a drilling and tapping step to form a hole matching the dimension of a fixture and a mount is coupled to the top portion of the fixture. The fixture and mount are implanted into the alveolar bone using an operation handpiece and the mount is removed from the fixture so that the fixture is implanted into the alveolar bone. A cover screw is coupled to the top portion of the fixture to suture the fixture so that the first operation is complete.

The cover screw prevents the intrusion of germs and foreign materials existing in the mouth until the fixture is completely osseointegrated. Although the period of the osseointegration varies according to the bone quality of a patient and the position of implantation, it typically takes three to six months.

Later, the gum is open by a second operation to expose the cover screw. The degree of osseointegration of the fixture is checked and the cover screw is removed. For the formation of an aesthetic gum, a healing abutment is coupled to the top portion of the fixture and two to three weeks are needed for completion. To simplify the second operation method, a first operation method can be used in which the steps of coupling and removing the cover screw are omitted and the healing abutment is directly coupled to the fixture.

After checking the formation of an aesthetic gum, the healing abutment is removed and an impression coping is coupled to the top portion of the fixture to manufacture a prosthesis. A preliminary impression is obtained in the mouth using an impression material and then the impression coping is removed.

A tooth model is manufactured and an artificial tooth, that is, an artificial crown, is processed. The abutment is coupled to the top portion of the fixture and the prosthesis, that is, the artificial crown, is fixed to the abutment so that the artificial tooth is completed.

As described above the healing abutment is used to form an aesthetic gum during the operation of an implant. Since the implant operation is widely performed and its technology is well known and has developed, the aesthetic result after the implant operation can be discussed among patients so that the aesthetic result after the implant operation becomes more important.

Figure 1:
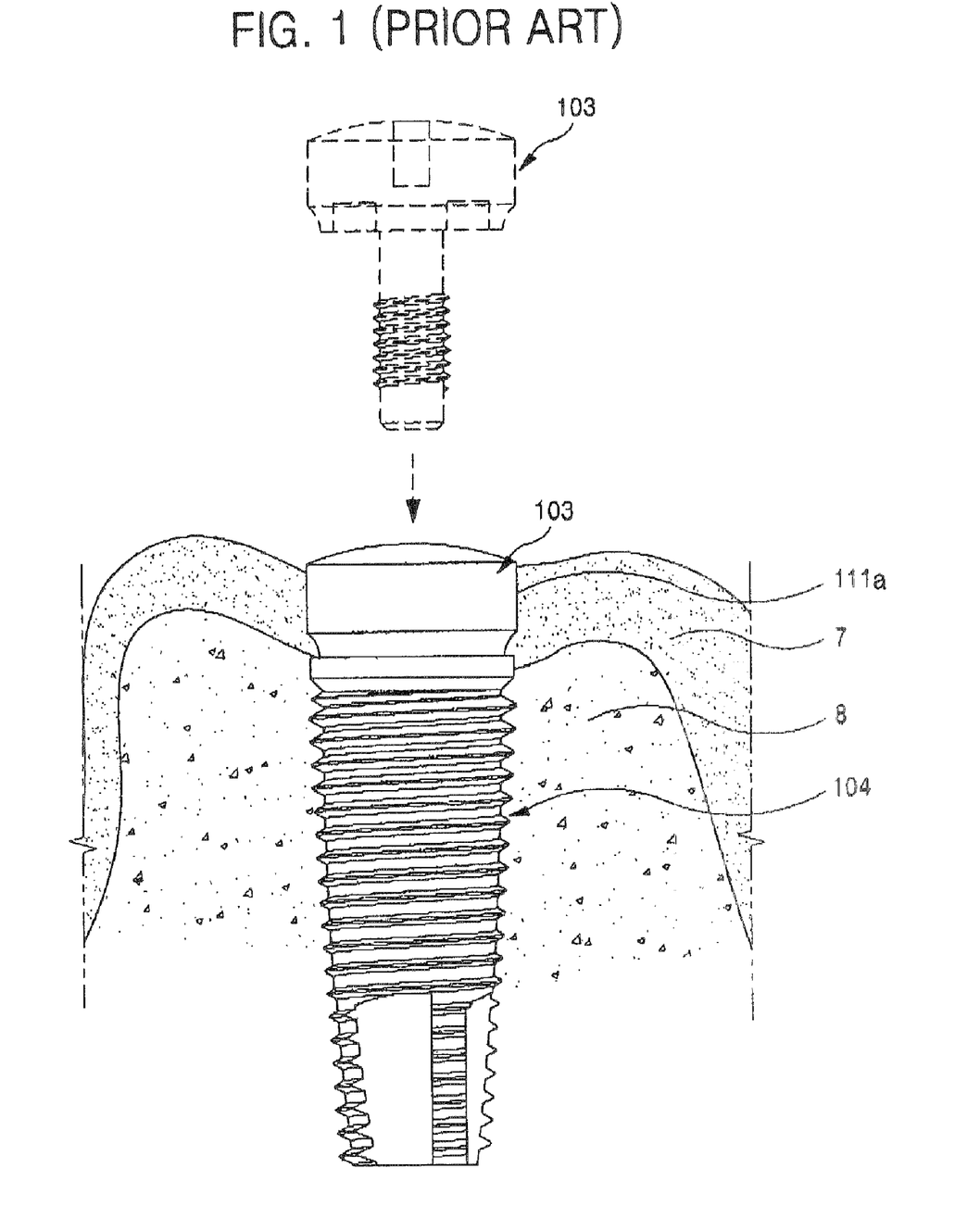
FIG. 1 is a view showing a conventional healing abutment that is coupled to a fixture.
Figure 2:
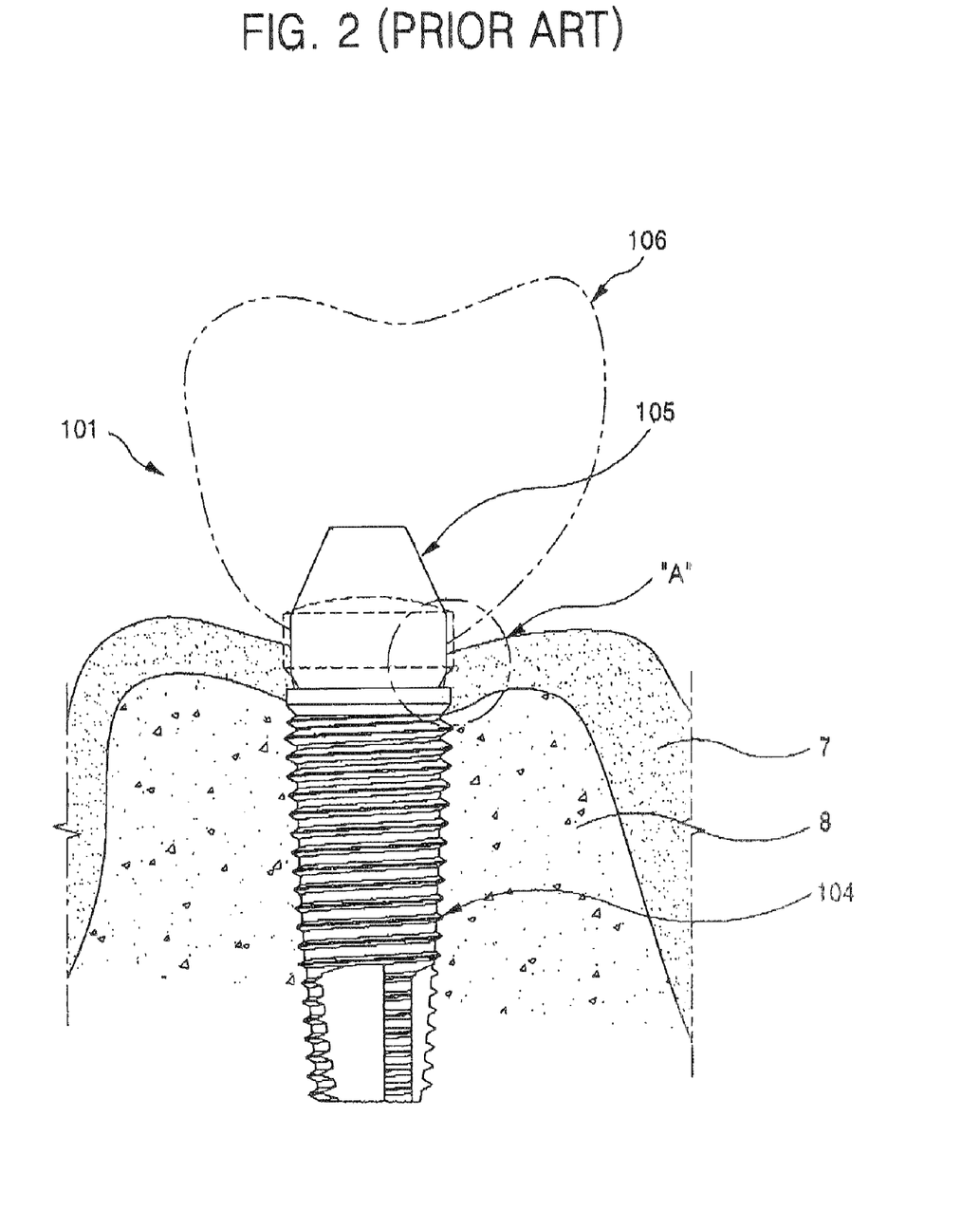
FIG. 2 is a view showing that the abutment and an artificial crown are coupled to the top portion of the fixture after the healing abutment of FIG. 1 is removed.

FIG. 1 is a view showing a healing abutment that is coupled to a fixture. FIG. 2 is a view showing the abutment and an artificial crown are coupled to the top portion of the fixture after the healing abutment of FIG. 1 is removed. As shown in FIGS. 1 and 2, a healing abutment 103 has a role of forming an aesthetic gum by being coupled to a fixture 104 implanted into an alveolar bone 8 before an artificial tooth is complete by installing an abutment 105 and fixing an artificial crown 106 on the abutment 105.

In the healing abutment 103, since a gum contact portion 111a of the healing abutment 103 that contacts a gum 7 has an outer diameter that increases from a lower end of the healing abutment 103 to an upper end thereof or the outer diameter of the healing abutment 103 is greater than that of the abutment 105 for the coupling of the artificial crown 106, as indicated by "A" of FIG. 2, after the operation of an implant 101 is complete, that is, the healing abutment 103 is removed the abutment 105 is coupled to the fixture 104, and the artificial crown 106 is fixed to the abutment 105, it is a problem that the gum 7 formed around the healing abutment 103 may collapse. Although the healing abutment 103 is used to form an aesthetic gum, the gum 7 is not maintained and collapses after the implant operation. The gum 7 collapses when a shape of the gum 7 is not closely contacting the implant 101. Further, metal of the implant 101 can be seen directly through a gap between the implant 101 and the gum 7 or reflected by a neighboring tooth so that a black line is formed between teeth, thus deteriorating the aesthetic feature.

Also, since germs or foreign materials may intrude through a gap between the gum 7 and the implant 101, which is generated as the gum 7 collapses, if the gum 7 collapses after the implant operation, teeth or the inside of the mouth can be contaminated.

Therefore, a need exists for a healing abutment and a dental implant having the same with an improved aesthetic feature.

SUMMARY OF THE INVENTION

According to an embodiment of the present invention, a healing abutment comprises a main body portion having an inclined section that is inclined such that at least a part of a gum contact portion that contacts a gum when coupled to a fixture that is implanted into an alveolar bone has an outer diameter that decreases from a lower end toward an upper end, and a coupling portion coupled to the main body portion to detachably couple the main body portion to the fixture.

When an abutment for the coupling of an artificial crown is coupled to the fixture, the gum around the abutment has a shape protruding further than the gum when contacting the main body portion.

The inclined section comprises a concave surface having a predetermined inward curvature in a radial direction from an outer surface of the main body portion.

The main body portion further comprises a wide linear section having an outer surface that is linear throughout a first predetermined length section from an area contacting an upper end of the fixture and an insertion groove formed inside the wide linear section into which a protruding portion formed on the upper end of the fixture is inserted.

An area where the inclined section and the wide linear section contact each other is rounded.

The main body portion further comprises a narrow linear section that is formed opposite to the wide linear section with respect to the inclined section, the narrow linear section having an outer surface which is linear throughout a second predetermined length section, and having a diameter smaller than that of the wide linear section.

A tool hole is formed in an upper end portion of the main body portion having a predetermined depth from an upper surface of the main body portion, wherein the tool hole comprises a screw portion where a screw is formed in a third predetermined length section so that an impression coping is detachable and a toot latch portion arranged close to the screw portion so that a tool is inserted in the screw portion.

An exposed upper end surface of the main body portion located opposite to the coupling portion is substantially flat to be coupled to an impression coping.

A corner of an upper end portion of the main body portion is rounded.

A maximum diameter of the main body portion is substantially the same as or less than a maximum diameter of the fixture.

The main body portion and the coupling portion are integrally formed.

According to another embodiment of the present invention, a dental implant comprises a fixture implanted into an alveolar bone, and a healing abutment for shaping a gum, the healing abutment coupled to the fixture before an abutment for the coupling of an artificial crown is coupled to the fixture, wherein the healing abutment comprises a main body portion having an inclined section that is inclined such that at least a part of a gum contact portion that contacts the gum when coupled to the fixture has an outer diameter that decreases from a lower end toward an upper end, and a coupling portion coupled to the main body portion to detachably couple the main body portion to the fixture.

When the abutment is coupled to the fixture, the gum around the abutment has a shape protruding further than the gum when contacting the main body portion of the healing abutment.

The inclined section comprises a concave surface having a predetermined inward curvature in a radial direction from an outer surface of the main body portion, and a maximum diameter of the main body portion is substantially the same as or less than a maximum diameter of the fixture.

A tool hole is formed in an upper end portion of the main body portion having a predetermined depth from an upper surface of the main body portion, wherein the tool hole comprises a screw portion where a screw is formed in a predetermined length section so that an impression coping is detachable and a tool latch portion arranged close to the screw portion so that a tool is inserted in the screw portion.

BRIEF DESCRIPTION OF THE DRAWINGS

The present invention will become more apparent by describing in detail preferred embodiments thereof with reference to the attached drawings in which.

DETAILED DESCRIPTION OF PREFERRED EMBODIMENTS

The attached drawings for illustrating preferred embodiments of the present invention are referred to in order to gain a sufficient understanding of the present invention, the merits thereof, and the objectives accomplished by the implementation of the present invention.

Hereinafter, the present invention will be described in detail by explaining preferred embodiments of the invention with reference to the attached drawings. Like reference numerals in the drawings denote like elements.

Figure 3:
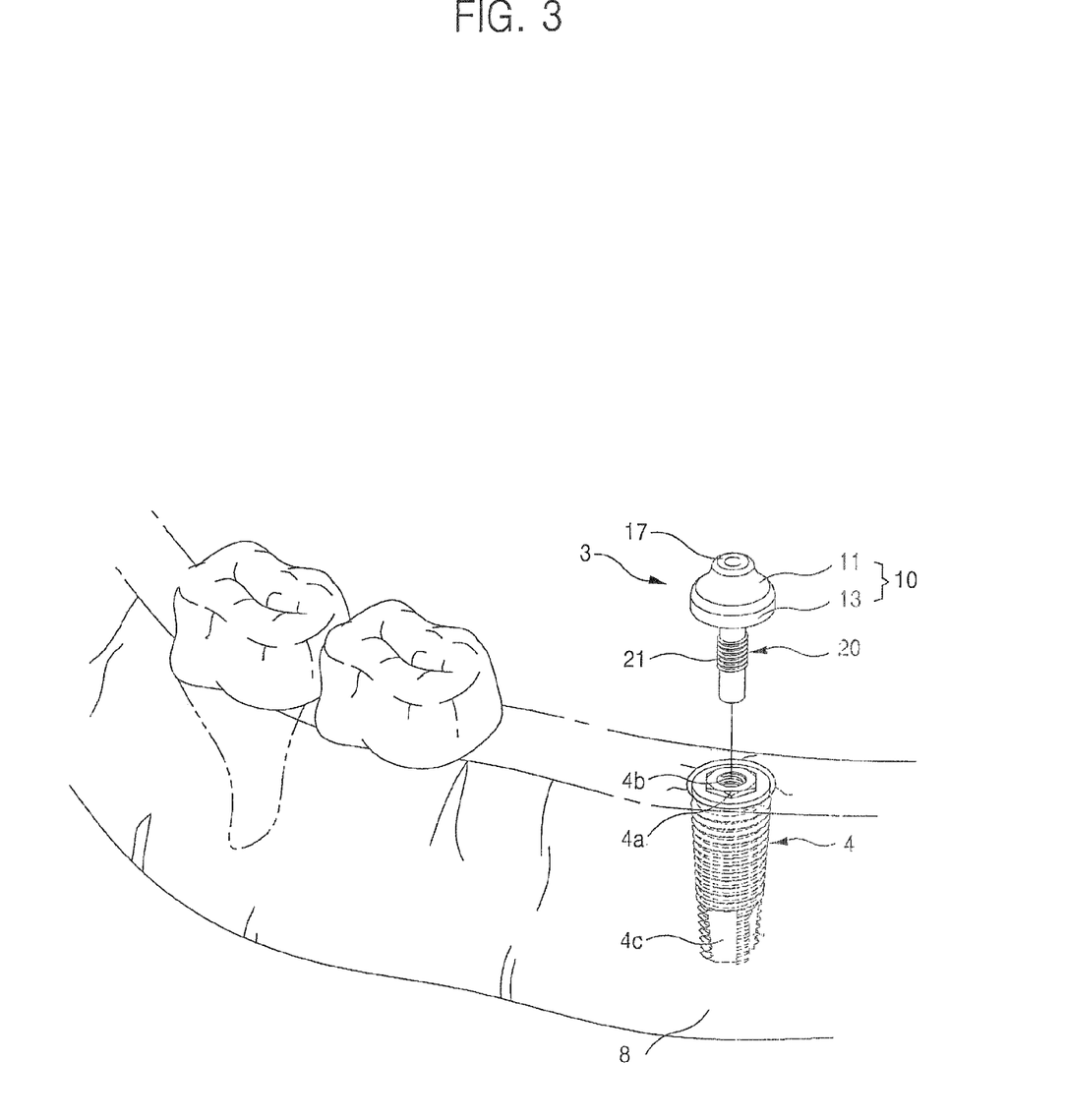
FIG. 3 is a perspective view showing that a healing abutment according to an embodiment of the present invention is coupled to a fixture.
Figure 4:
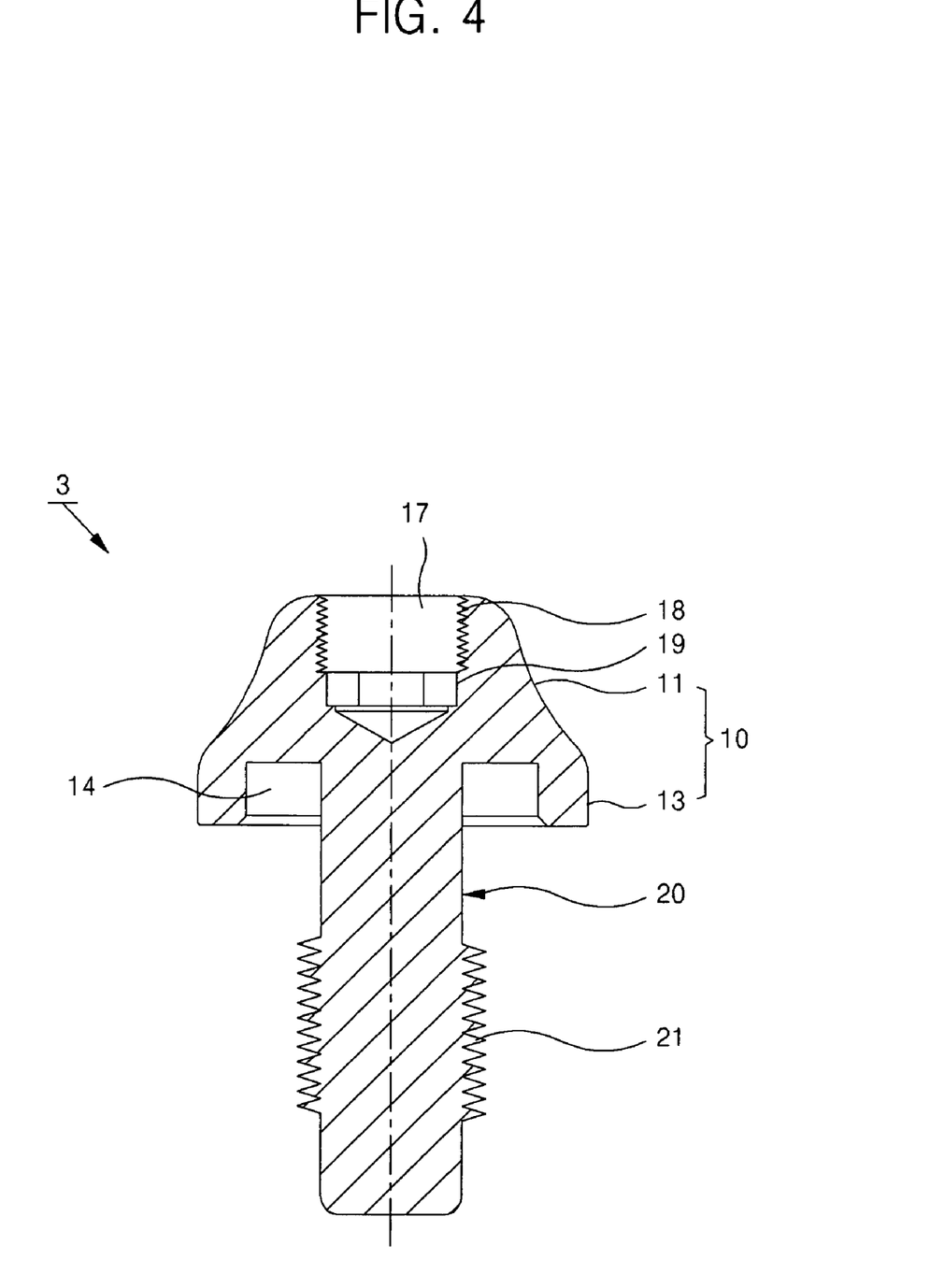
FIG. 4 is a cross-sectional view of the healing abutment of FIG. 3.
Figure 5:
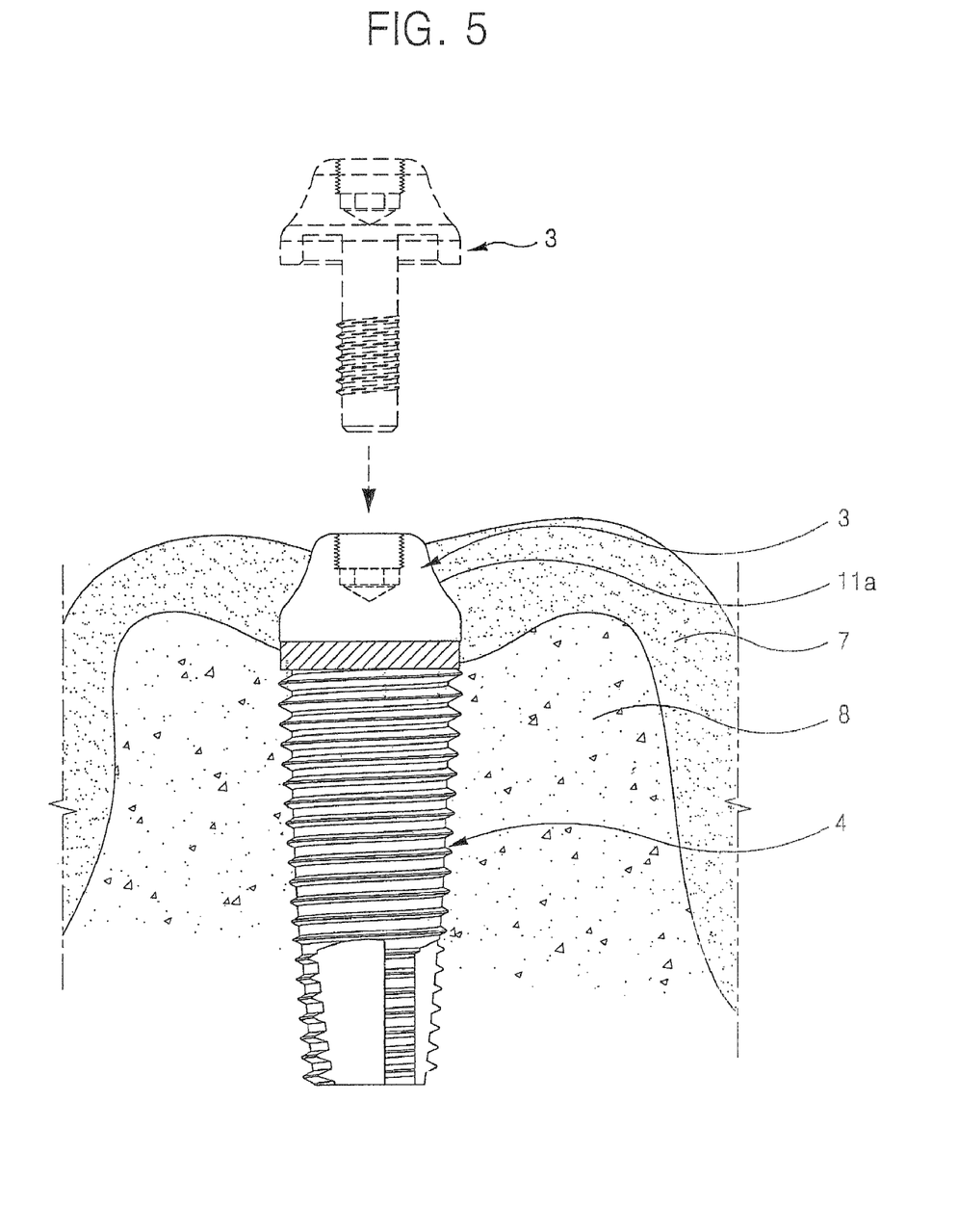
FIGS. 5 through 7 are views for explaining the step of an implant operation using a dental implant having the healing abutment of FIG. 3.
Figure 6:
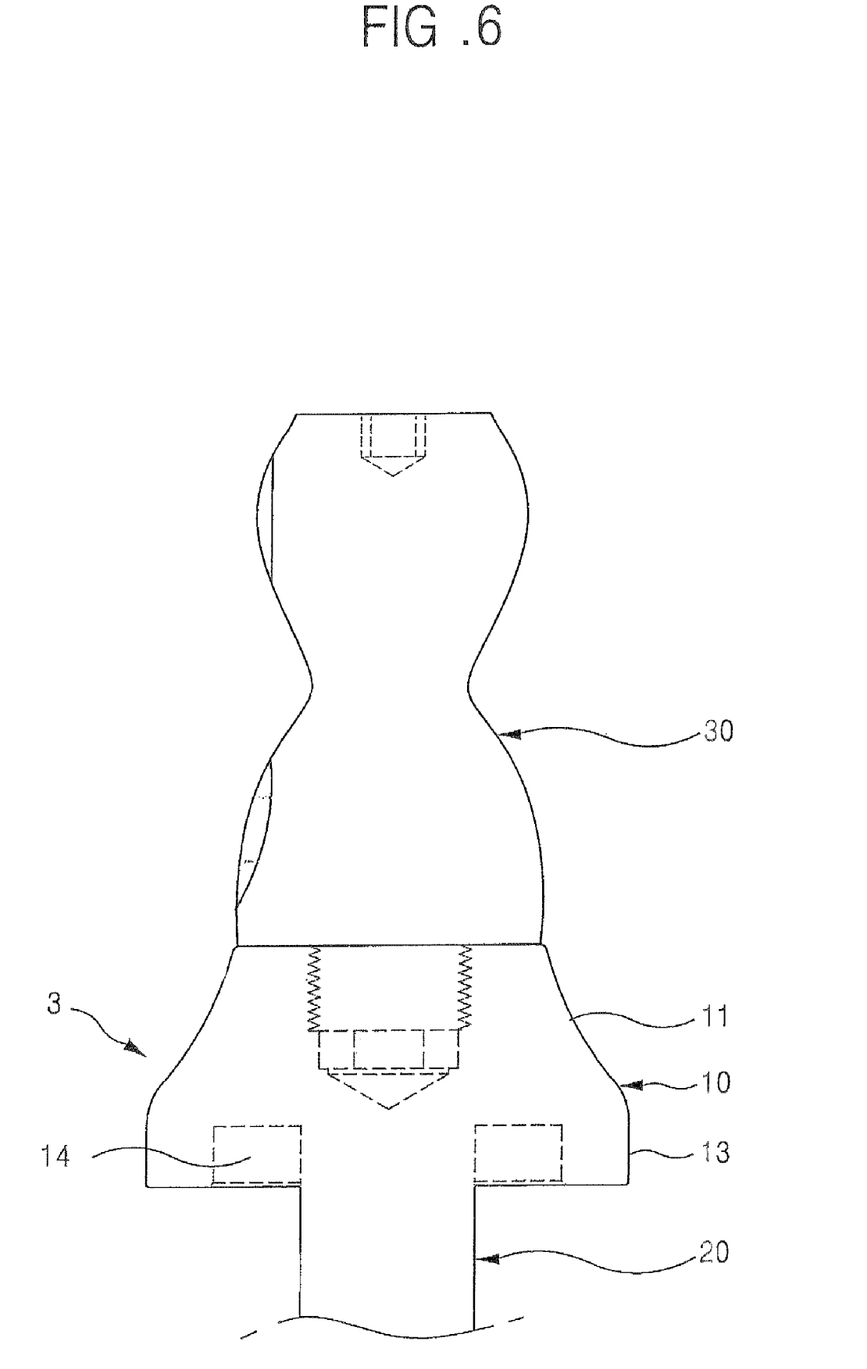
Figure 7:
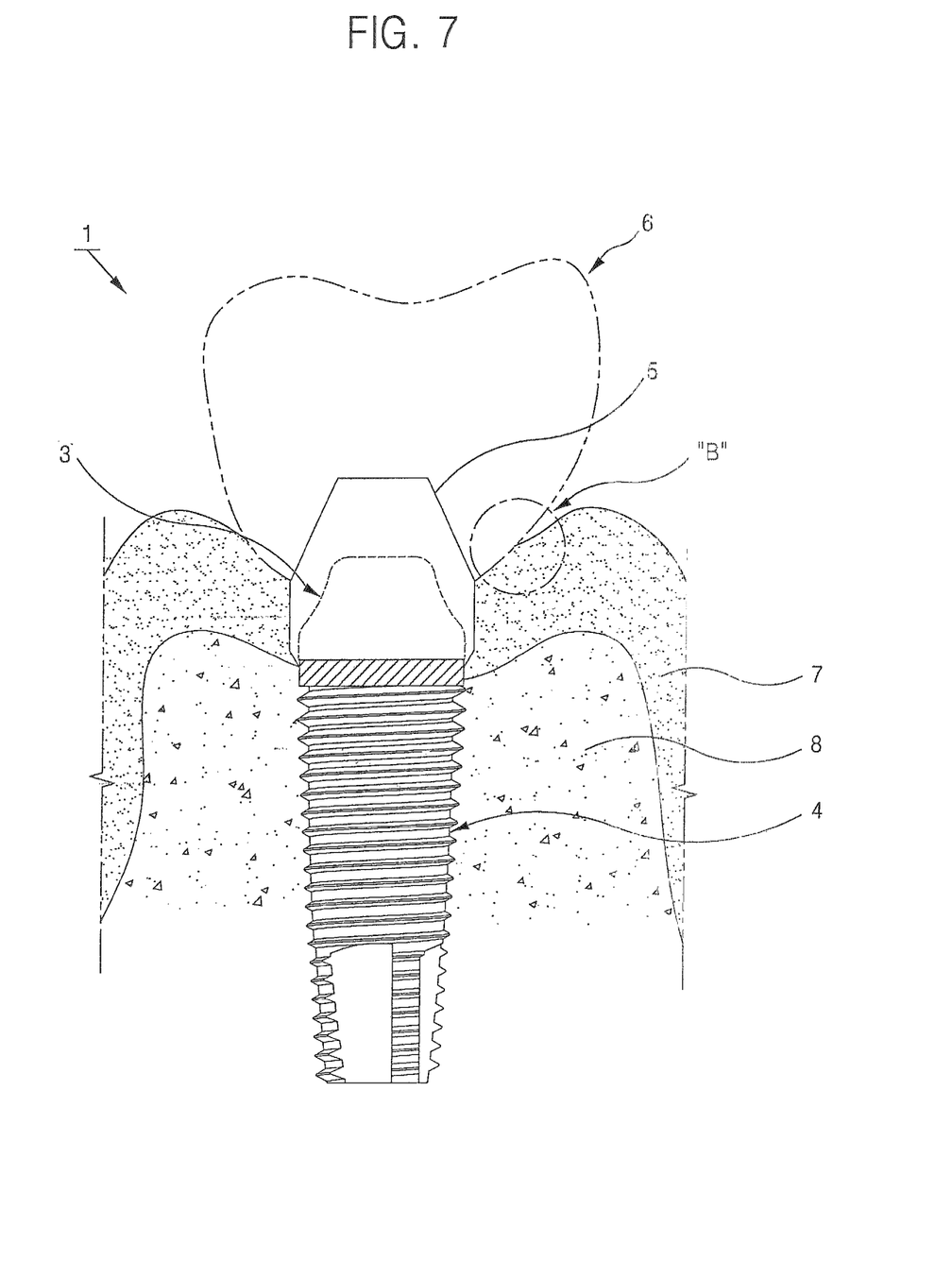

FIG. 3 is a perspective view showing that a healing abutment according to an embodiment of the present invention is coupled to a fixture. FIG. 4 is a cross-sectional view of the healing abutment of FIG. 3. FIGS. 5 through 7 are views for explaining an implant operation using a dental implant having the healing abutment of FIG. 3.

As shown in FIGS. 3 through 7, a healing abutment 3 according to an embodiment of the present invention includes a main body portion 10 and a coupling portion 20 coupled to the main body portion 10. The coupling portion 20 detachably couples the main body portion 10 to a fixture 4. The main body portion 10 includes an inclined section 11 and a wide linear section 13. The inclined section 11 is inclined such that at least a part of a gum contact portion 11a that contacts a gum when coupled to the fixture 4 that is implanted into an alveolar bone has an outer diameter that decreases from a lower end toward an upper end. The wide linear section 13 extends from the lower portion of the inclined section 11.

The inclined section 11 is concave, having a predetermined inward curvature in a radial direction from an outer surface of the main body portion 10. The inclined section 11 is the gum contact portion 11a that contacts the gum 7 and has an inwardly concave shape. This structure enables the gum 7 to have an improved aesthetic feature after an implant operation.

The gum 7 formed around the healing abutment 3 according to an embodiment of the present embodiment is pushed to both sides as shown in FIG. 7 when the abutment 5 for the coupling of the artificial crown 6 is coupled to the fixture 4. The abutment 5 has a large volume in an area contacting the gum 7 and the gum 7 is a soft tissue that enables a certain degree of contraction and expansion. Thus the gum 7 around the abutment 5, which is formed as the gum 7 is pushed to both sides when the abutment 5 is coupled to the fixture 4, protrudes upwardly to be higher than the gum 7 when the healing abutment 3 is coupled to the fixture 4.

Gum 7 collapse after the implant operation and the resulting metal or black line appearing due to the low height of the gum 7, can be substantially prevented, and an aesthetic feature after the implant operation is improved. Also, as the gap between the implant 1 and the gum 7 is substantially blocked, and the intrusion of germs or foreign materials can be substantially prevented.

The wide linear section 13 extending from the lower portion of the inclined section 11 has an outer surface that is linear in a predetermined length section from an area contacting the upper end of the fixture 4 when the healing abutment 3 is coupled to the fixture 4. An insertion groove 14, into which a protruding portion 4a formed on the upper end of the fixture 4 is inserted, is formed inside the wide linear section 13. When the healing abutment 3 is coupled to the fixture 4, the protruding portion 4a of the fixture 4 is inserted in the insertion groove 14 formed inside the wide linear section 13.

The main body portion 10 includes the inclined section 11 and the wide linear section 13 as described above, and may further include a narrow linear section 15 extending from the upper end of the inclined section 11 according to another embodiment of the present invention. The narrow linear section 15 will be described below in detail.

In the main body portion 10 of the healing abutment 3, it can be seen that the maximum diameter of the main body portion 10 is substantially the same as or less than that of the fixture 4. Thus, when the gum 7 is formed using the healing abutment 3, the gum 7 formed by the healing abutment 3 needs to be slightly pushed to both sides so that the gum 7 is convex after the implant operation is complete, providing an aesthetic feature. Also, since no gap is formed between the gum 7 and the implant 1, the intrusion of germs or foreign materials can be substantially prevented.

Since the healing abutment 3 is coupled to and removed from the fixture 4 in the implant operations the healing abutment 3 passes through the gum 7 during the operation. Thus, the healing abutment 3 has a soft surface to substantially prevent damage to the gum 7 as the healing abutment 3 contacts the gum 7 during the operation. In addition, since the healing abutment 3 needs to be coupled to the fixture 4 for a predetermined period of time, a soft feeling is achieved whenever a tongue touches the healing abutment 3. To this end, in the healing abutment 3 according to an embodiment of the present invention, an area where the inclined section 11 and the wide linear section 13 of the main body portion 10 contact each other or the upper end portion of the main body portion 10, that is, a corner of the upper end portion of the inclined section 11, is rounded.

The implant operation includes a prosthesis step in which an artificial tooth, that is, the artificial crown 6, is installed above the fixture 4. The artificial crown 6 can be accurately manufactured in dental laboratory only when the situation of the inside of a mouth is presented as it is in the prosthesis step. To this end, a model reflecting the situation of the inside of the mouth is manufactured and an impression needs to be obtained to manufacture such a model.

When a two-piece abutment is used in which a screw connecting the abutment 5 and the fixture 4 is separately manufactured and connected therebetween, implant manufacturers recommend that an impression body be obtained in the form of a fixture level impression for the process of dental laboratory. In the fixture level impression method, an impression coping 30 is connected within the mouth.

According to an embodiment of the present invention, a tool hole 17 is formed in the top portion of the main body portion 10 and has a screw portion 18 over a predetermined length section so that the impression coping 30 is detachable from the abutment 3 and a tool latch portion 19 in which a tool for rotating the healing abutment 3 is inserted when the healing abutment 3 is coupled to the fixture 4. The tool latch portion 19 is typically provided as a hexagonal hole. The screw portion 18 having a diameter greater than the tool latch portion 19 is provided above the tool latch portion 19 so that a screw provided at the impression coping 30 is coupled thereto. Although the screw portion 18 is depicted above the tool latch portion 19, the screw portion 18 is not limited thereto. For example, the screw portion 18 having a diameter smaller than the tool latch portion 19 can be provided under the tool latch portion 19.

As the screw portion 18 and the tool latch portion 19 are provided in the tool hole 17, when the healing abutment 3 is coupled to the fixture 4, the tool is coupled to the tool latch portion 19 while passing the screw portion 18. As the healing abutment 3 is rotated by the tool, the healing abutment 3 is coupled to the fixture 4. When impression is obtained, the impression coping 30 is coupled to the screw portion 18 of the tool hole 17 of the healing abutment 3.

In the healing abutment 3 according to an embodiment of the present embodiment, the exposed upper end surface of the main body portion 10 located opposite to the coupling portion 20 is processed to be flat for the coupling of the impression coping 30. When the impression coping 30 is manufactured such that the lower surface of the impression coping 30 has a diameter corresponding to the healing abutment 3 whose exposed upper surface of the main body portion 10 has the minimum diameter, a single impression coping can be used for a variety of healing abutments. Accordingly, the impression coping 30 can be used regardless of the type of the fixture 4 or the healing abutment 3 in use.

The coupling portion 20 is coupled to the main body portion 10 and detachably couples the main body portion 10 to the fixture 4. Thus, a screw 21 that is screw-coupled to a screw hole 4b in the upper end portion of the fixture 4 is formed on the coupling portion 20. Although the coupling portion 20 is depicted as being integrally formed with the main body portion 10, it may be separately provided and coupled to the main body portion 10.

The fixture 4, to which the healing abutment 3 is coupled, is implanted in the alveolar bone 8. The fixture 4 is osseointegrated to the alveolar bone 8 to be completely fixed thereto like a root of a nature tooth. After the osseointegration, the abutment 5 is connected to the fixture 4 and the artificial crown 6 is installed thereon so that an implant artificial tooth is completed. The fixture is typically made of pure titanium or a titanium alloy, or metal showing no rejection symptoms in a human body, or reactions to a metal alloy, or ceramic.

As described above, the protruding portion 4a having a hexagonal screw head shape to accurately couple the healing abutment 3 is provided on the upper surface of the fixture 4 of FIG. 3. The screw hole 4b is axially extended from the center of the protruding portion 4a and coupled to the screw 21 of the coupling portion 20 of the healing abutment 3. Here, the protruding portion 4a is inserted into the insertion groove 14 formed inside the wide line section 13 of the healing abutment 3.

The length of the fixture 4 of the implant may vary between about 8-19 mm according to the clinical situation. Four self tapping grooves 4c are formed at the lower end portion of the fixture 4 and symmetrically arranged with respect to the center axis for self tapping when the fixture 4 is inserted into a hole in the alveolar bone 8. Although four self tapping grooves 4c are depicted, the scope of right of the present invention is not limited thereto and the number of the self tapping grooves may be, for example, three according to the situation.

The step of performing an implant operation using an implant having a healing abutment according to an embodiment of the present invention will be described with reference to FIGS. 3 through 7.

A hole is formed in the alveolar bone 8 in a mouth subject to an operation to match the dimension of the fixture 4 through drilling and tapping steps. The fixture 4 is implanted in the hole of the alveolar bone 8. A cover screw (not shown) is coupled to the top portion of the fixture 4 to suture the fixture 4, completing the first operation. The period of osseointegration is typically three to six months, although the period varies according to the bone quality of a patient and the position of implantation.

Through the second operation the gum 7 is opened to expose the cover screw and the degree of osseointegration of the fixture 4 is checked and the cover screw is removed. To form an aesthetic gum, the healing abutment 3 is coupled to the upper portion of the fixture 4. In dosing so, to simplify the second operation method, while the steps of coupling and removing the cover screw may be omitted, wherein the healing abutment 3 can be coupled to the fixture 4 during the first operation in which the fixture 4 is implanted.

When the healing abutment 3 is coupled to the fixture 4, the screw 21 of the coupling portion 20 of the healing abutment 3 is coupled to the screw hole 4b formed in the fixture 4. Also, the protruding portion 4a on the upper surface of the fixture 4 is coupled to the insertion groove 14 provided in the lower portion of the healing abutment 3. Thus, the healing abutment 3 and the fixture 4 are accurately coupled to each other.

To maintain the shape of the gum 7, the gum 7 around the healing abutment 3 is sutured using a suturing thread. Since the diameter of the upper end of the healing abutment 3 according to an embodiment of the present embodiment is small, the suturing of the gum 7 is limited and the gum 7 appears aesthetic. After the suturing step, a predetermined period of time is needed for the formation of an aesthetic gum. During the period of time for the formation of the aesthetic gum, the gum 7 around the healing abutment 3 closely contacts the shape of the healing abutment 3. Here, since the healing abutment 3 according to an embodiment of the present embodiment includes the inclined section 11 that is concave at the predetermined inward curvature in a radial direction from the outer surface of the main body portion 10, the gum 7 of a soft tissue takes the shape of the healing abutment 3, while closely contacting the same.

After the formation of an aesthetic gum is checked, the impression coping 30 is coupled to the screw portion 18 on the flat top portion of the healing abutment 3 as shown in FIG. 6 and impression in the mouth is obtained using an impression material and the impression coping 30 is removed. The healing abutment 3, according to an embodiment of the present embodiment in which the upper surface thereof is flat, enables a single impression coping coupled to a variety of healing abutments. Also, since the screw portion 18 is provided in the upper end portion of the healing abutment 3, the impression of the mouth can be obtained by coupling the impression coping 30 directly to the healing abutment 3 without removing the healing abutment 3.

After a tooth model is manufactured and an artificial tooth, that is, the artificial crown 6, is processed, the healing abutment 3 is removed from the fixture 4. Then, the abutment 5 is coupled to the top portion of the fixture 4 and a prosthesis, that is, the artificial crown 6, is fixed to the abutment 5 so that the artificial tooth is complete.

When the abutment 5 is coupled to the top portion of the fixture 4, the abutment 5 is pushed into an opening of the gum 7 that is formed around the healing abutment 3 and coupled to the upper surface of the fixture 4. Since the space occupied by the abutment 5 is larger than that occupied by the healing abutment 3, as shown in FIG. 7, when the abutment 5 is coupled to the fixture 4, the abutment 5 pushes the gum 7 to the outside. As a result as indicated by "B" in FIG. 7, the soft gum 7 closely contacts the outer surface of the abutment 5 and/or the artificial crown 6 and protrudes upward so that an aesthetic appearance is obtained.

According to an embodiment of the present embodiment, since the protruding shape of the gum 7 after the implant operation is maintained and closely contacts the artificial tooth, an aesthetic feature can be obtained. Also, since the gap between the gum 7 and the abutment 5, or between the gum 7 and the artificial crown 6, is blocked by the gum 7, the intrusion of germs or foreign materials in the mouth can be effectively prevented.

A healing abutment according to another embodiment of the present invention will be described below with reference to the accompanying drawings. In the following description, the same constituent elements and operations that are the same as those of the previously described embodiment will be omitted.

Figure 8:
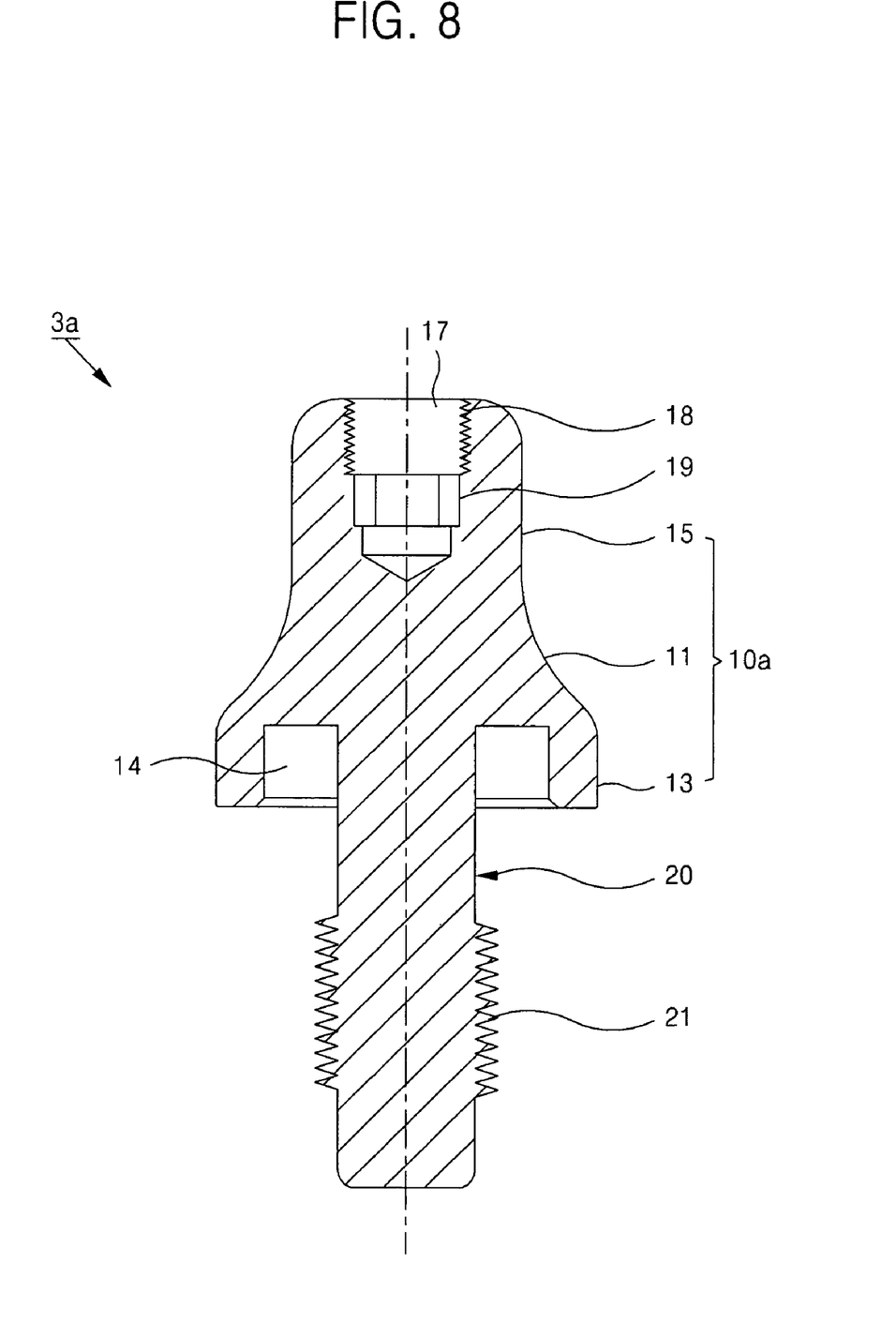
FIG. 8 is a cross-sectional view of a healing abutment according to another embodiment of the present invention.

FIG. 8 is a cross-sectional view of a healing abutment according to another embodiment of the present invention. Referring to FIG. 8, the main body 10 of a healing abutment 3a according to another embodiment of the present invention further includes a narrow linear section 15 extending upward from the inclined section 11.

Since the fixture 4 of an implant is manufactured in a variety of sizes according to the position in the mouth the healing abutment 3 also may be formed in a variety of sizes. For example, when the diameter of the fixture 4 to which the healing abutment 3a according to an embodiment of the present embodiment is coupled is less than that of the fixture 4 according to previously described embodiments, the height of the healing abutment 3a is typically greater than that of the healing abutment 3. In this case, the healing abutment 3a further includes the narrow linear section 15.

Although in above-described embodiments the main body portion may further include the wide linear section in addition to the inclined section or the wide linear section and the narrow linear section, in some cases, the main body portion can be formed with only the inclined section. Also, although in above-described embodiments the inclined section of the main body portion is concave at a predetermined inward curvature in a radial direction from the outer surface thereof, the inclined section of the main body portion may be formed linear.

While this invention has been particularly shown and described with reference to preferred embodiments thereof, it will be understood by those skilled in the art that various changes in form and details may be made therein without departing from the spirit and scope of the disclosure.

As described above according to an embodiment of the present invention, the gum does not collapse after the implant operation and a convex shape can be maintained. Thus, an aesthetic feature is obtained. Furthermore, since the gap between the gum and the implant is substantially blocked, the intrusion of germs or foreign materials can be substantially prevented.

What is claimed is:

1. An apparatus comprising:
a main body portion coupled to a fixture for implantation into an alveolar bone, the main body portion having an inclined section that is inclined such that at least a part of a gum contact portion is adapted to contact a gum, the gum contact portion having an outer diameter that decreases from a lower end toward an upper end; and
a coupling portion integrally formed with the main body portion to detachably couple the main body portion to the fixture,
wherein a tool hole is formed in an upper end portion of the main body portion having a predetermined depth from an upper surface of the main body portion, wherein the tool hole comprises:
a screw portion where threads are formed in a third predetermined length section so that an impression coping is detachable; and
a tool latch portion arranged close to the screw portion so that a tool is inserted in the tool latch portion,
wherein the inclined section comprises a concave surface having a predetermined inward curvature in a radial direction from an outer surface of the main body portion, and
wherein a topmost corner of an upper end portion of the main body portion is rounded.

2. The apparatus of claim 1, wherein the main body portion further comprises:
a wide linear section having an outer surface that is linear throughout a first predetermined length section from an area contacting an upper end of the fixture; and
an insertion groove formed inside the wide linear section into which a protruding portion formed on the upper end of the fixture is inserted.

3. The apparatus of claim 2, wherein an area where the inclined section and the wide linear section contact each other is rounded.

4. The apparatus of claim 2, wherein the main body portion further comprises a narrow linear section that is formed opposite to the wide linear section with respect to the inclined section, the narrow linear section having an outer surface which is linear throughout a second predetermined length section, and having a diameter smaller than that of the wide linear section.

5. The apparatus of claim 1, wherein an exposed upper end surface of the main body portion located opposite to the coupling portion is substantially flat to be coupled to an impression coping.

6. The apparatus of claim 1, wherein a maximum diameter of the main body portion is substantially the same as or less than a maximum diameter of the fixture.

7. The apparatus of claim 1, further comprising the impression coping detachably coupled to the main body portion via the screw portion.

8. An apparatus comprising:
a fixture adapted to be implanted into an alveolar bone; and
a healing abutment for shaping a gum, the healing abutment coupled to the fixture before an abutment for the coupling of an artificial crown is coupled to the fixture,
wherein the healing abutment comprises:
a main body portion coupled to the fixture, the main body portion having an inclined section that is inclined such that at least a part of a gum contact portion is adapted to contact the gum, the gum contact portion having an outer diameter that decreases from a lower end toward an upper end; and
a coupling portion integrally formed with the main body portion to detachably couple the main body portion to the fixture,
wherein a tool hole is formed in an upper end portion of the main body portion having a predetermined depth from an upper surface of the main body portion, wherein the tool hole comprises:
a screw portion where threads are formed in a third predetermined length section so that an impression coping is detachable; and
a tool latch portion arranged close to the screw portion so that a tool is inserted in the tool latch portion,
wherein the inclined section comprises a concave surface having a predetermined inward curvature in a radial direction from an outer surface of the main body portion,
wherein a topmost corner of an upper end portion of the main body portion is rounded, and
wherein a maximum diameter of the main body portion is substantially the same as or less than a maximum diameter of the fixture.

9. The apparatus of claim 8, further comprising the impression coping detachably coupled to the main body portion via the screw portion.

* * * * *